(12) United States Patent
Neves et al.

(10) Patent No.: US 11,324,700 B2
(45) Date of Patent: May 10, 2022

(54) METHOD OF PRODUCTION OF INHALABLE COMPOSITE PARTICLES USING A THREE-FLUID NOZZLE

(71) Applicant: Hovione Scientia Limited, Cork (IE)

(72) Inventors: Filipe Neves, Lisbon (PT); Claudia Moura, Lisbon (PT); Eunice Costa, Lisbon (PT)

(73) Assignee: Hovione Scientia Limited, Cork (IE)

( * ) Notice: Subject to any disclaimer, the term of this patent is extended or adjusted under 35 U.S.C. 154(b) by 0 days.

(21) Appl. No.: 15/767,245

(22) PCT Filed: Oct. 12, 2016

(86) PCT No.: PCT/GB2016/053158
§ 371 (c)(1),
(2) Date: Apr. 10, 2018

(87) PCT Pub. No.: WO2017/064481
PCT Pub. Date: Apr. 20, 2017

(65) Prior Publication Data
US 2019/0076360 A1    Mar. 14, 2019

(30) Foreign Application Priority Data
Oct. 12, 2015 (PT) .......................... 108885

(51) Int. Cl.
| | | |
|---|---|---|
| A61K 9/16 | (2006.01) | |
| A61K 9/00 | (2006.01) | |
| A61K 9/50 | (2006.01) | |
| A61K 9/14 | (2006.01) | |
| A61K 31/56 | (2006.01) | |

(52) U.S. Cl.
CPC .......... *A61K 9/1623* (2013.01); *A61K 9/0073* (2013.01); *A61K 9/141* (2013.01); *A61K 9/1682* (2013.01); *A61K 9/1694* (2013.01); *A61K 9/50* (2013.01); *A61K 31/56* (2013.01)

(58) Field of Classification Search
None
See application file for complete search history.

(56) References Cited

U.S. PATENT DOCUMENTS

| | | |
|---|---|---|
| 4,610,760 A | 9/1986 | Kirkpatrick et al. |
| 7,862,834 B2 | 1/2011 | Vehring et al. |
| 8,668,934 B2 | 3/2014 | Vehring et al. |
| 2002/0132011 A1 | 9/2002 | Gordon et al. |
| 2005/0158386 A1 | 7/2005 | Tanno et al. |
| 2013/0266653 A1 | 10/2013 | Lipp et al. |

FOREIGN PATENT DOCUMENTS

| | | | |
|---|---|---|---|
| CN | 103841960 A | 6/2014 | |
| EP | 3037087 A1 * | 6/2016 | ............. A23K 40/30 |
| EP | 3037087 A1 | 6/2016 | |
| PT | 108885 | 10/2015 | |
| WO | 03037303 A1 | 5/2003 | |
| WO | WO-2008056344 A2 * | 5/2008 | ............. A61K 9/5036 |
| WO | 2013016754 A1 | 2/2013 | |
| WO | WO-2013016754 A1 * | 2/2013 | ............. A61K 9/1623 |
| WO | 2015025979 A1 | 2/2015 | |
| WO | 2017064481 A1 | 4/2017 | |

OTHER PUBLICATIONS

Sigma, Product Information, Insulin, Human, Recombinant Expressed in *E. coli*, Product No. I0259 and I2767, available at https://www.sigmaaldrich.com/content/dam/sigma-aldrich/docs/Sigma/Product_Information_Sheet/2/i2767pis.pdf, accessed on Nov. 9, 2020.*

Foreign Communication from a related application—International Search Report and Written Opinion of the International Searching Authority of Application No. PCT/GB2016/053158, dated Jan. 17, 2017, 13 pages.

Foreign Communication from a related application—Written Opinion of the International Preliminary Examining Authority of Application No. PCT/GB2016/053158, dated Oct. 11, 2017, 7 pages.

Foreign Communication from a related application—International Preliminary Report on Patentability of Application No. PCT/GB2016/053158, dated Feb. 1, 2018, 12 pages.

Jiang, Hao, et al., "Microencapsulation of α-Amylase by Carrying Out Complex Coacervation and Drying in a Single Step Using a Novel Three-Fluid Nozzle Spray Drying," Drying Technology, 2013, pp. 1901-1910, vol. 31, Taylor & Francis Group, LLC.

Kondo, Keita, et al., "Preparation of sustained-release coated particles by novel microencapsulation method using three-fluid nozzle spray drying technique," European Journal of Pharmaceutical Sciences, 2014, pp. 11-19, vol. 51, Elsevier B.V.

Legako, Jerrad, et al., "Effect of Spray Nozzle Design on Fish Oil—Whey Protein Microcapsule Properties," Journal of Food Science, 2010, pp. E394-E400, vol. 75, No. 6, Institute of Food Technologists.

Pabari, Ritesh M., et al., "Investigation of a novel 3-fluid nozzle spray drying technology for the engineering of multifunctional layered microparticles," Expert Opinion on Drug Delivery, 2012, 31 pages.

Palakodaty, Srinivas, et al., "Phase Behavioral Effects on Particle Formation Processes Using Supercritical Fluids," Pharmaceutical Research, 1999, pp. 976-985, vol. 16, No. 7, Plenum Publishing Corporation.

(Continued)

*Primary Examiner* — H. Sarah Park
(74) *Attorney, Agent, or Firm* — Conley Rose, P.C.; Rodney B. Carroll

(57) ABSTRACT

A method of preparing a pharmaceutical formulation which is suitable for inhalation, the method comprising: providing a solution comprising a first solvent or mixture of solvents and a poorly water soluble active agent; providing a second solution comprising a second solvent or mixture of solvents and an excipient. The first and second solvents or mixture of solvents are removed by simultaneously drying both solutions in a spray dryer equipped with a three-fluid nozzle to produce particles comprising an active agent and an excipient.

20 Claims, 3 Drawing Sheets

(56) References Cited

OTHER PUBLICATIONS

Son, Yoen-Ju, et al., "Preparation of sustained release rifampicin microparticles for inhalation," Journal of Pharmacy and Pharmacology, 2012, pp. 1291-1302, vol. 64, Journal of Pharmacy and Pharmacology.
Sou, Tomás, et al., "The effect of amino acid excipients on morphology and solid-state properties of multi-component spray-dried formulations for pulmonary delivery of biomacromolecules," European Journal of Pharmaceutics and Biopharmaceutics, 2013, pp. 234-243, vol. 83, Elsevier B.V.
Wan, Feng, et al., "One-Step Production of Protein-Loaded PLGA Microparticles via Spray Drying Using 3-Fluid Nozzle," Pharm Res, 2014, pp. 1967-1977, vol. 31, Springer.
Wang, Chenchen, et al., "Isoxyl particles for pulmonary delivery: In vitro cytotoxicity and potency," International Journal of Pharmaceutics, 2010, pp. 99-104, vol. 396, Elsevier B.V.
Foreign Communication from the priority application—Search Report of Portuguese Patent Application No. 108885 dated Jul. 27, 2016, in Portuguese language, 3 pages.
Foreign communication from a related application—First Office Action of Chinese Patent Application No. 201680066591.X dated Jul. 30, 2020, with English translation, 28 pages.

\* cited by examiner

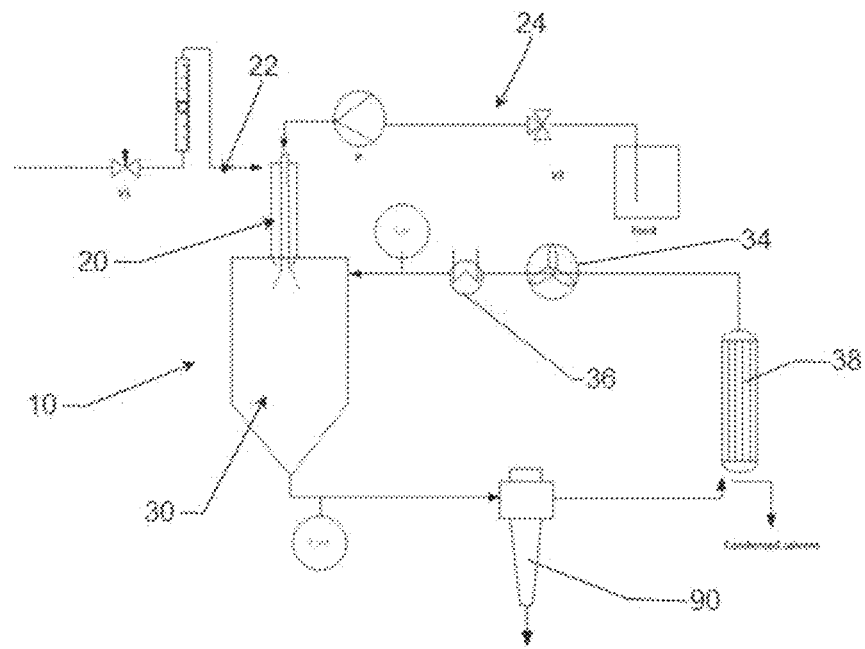
*FIG. 2 - PRIOR ART*
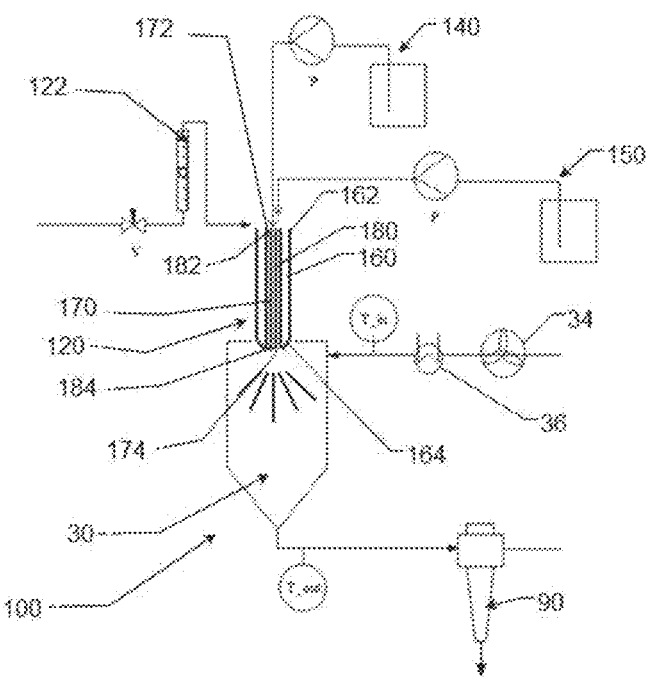
FIG. 3

METHOD OF PRODUCTION OF INHALABLE COMPOSITE PARTICLES USING A THREE-FLUID NOZZLE

CROSS REFERENCE TO RELATED APPLICATIONS

This application is a filing under 35 U.S.C. 371 of International Application No. PCT/GB2016/053158 filed Oct. 12, 2016, entitled "Method of Production of Inhalable Composite Particles using a Three-Fluid Nozzle" which claims priority to Portuguese Patent Application No. 108885 filed Oct. 12, 2015, which applications are incorporated by reference herein in their entirety.

BACKGROUND OF THE INVENTION

The present invention is in the technical field of drying methods for pharmaceutical compounds. More particularly, the present invention is in the technical field of spray drying applied to the production of inhalable composite particles comprising an active pharmaceutical ingredient (API) wherein the potential solubility differences and/or chemical incompatibility existing between the API and the excipient can be challenging when preparing a single solution. The present invention consists of a method of production of composite particles comprising an active agent and an excipient using spray drying apparatus having a three-fluid nozzle. The active agent can be one or more APIs and can be poorly water soluble, and the excipient can be one or more excipients.

In the pharmaceutical industry there is a wide variety of drug delivery platforms, namely for oral delivery through tablets, pills, capsules, elixirs, or the like; for topical, injectable, ocular and orally or nasally inhaled delivery among others. Pharmaceutical interest in the delivery of drugs to the lungs has been increasing, either to treat local diseases such as asthma, chronic obstructive pulmonary diseases (COPD), emphysema and cystic fibrosis, or for systemic drug delivery to treat diabetes, osteoporosis, cancer, neurological diseases (including pain) or prophylaxis of a disease, among others. Drug delivery to the lungs presents several advantages due to the advantageous physiological characteristics of the lungs such as low enzymatic activity and thin epithelial barrier to absorption. Some of the advantages are the rapid onset of drug action and bioavailability, while avoiding the first pass metabolism which reduces the total drug load required and minimizes the adverse side effects, leading to a more efficient therapy for the patients.

There are many types of inhaler devices able to deliver the APIs as a dry powder or in a liquid, namely, dry powder inhalers (DPIs), pressurized metered dose inhalers and nebulizers. The DPI can be active or passive and the drug can be administered as a unit-dose or a multi-dose reservoir, actuated at different flowrates, pressures and aerosolization mechanisms according to the device design.

The present invention produces a DPI formulation using a new production method which utilizes a spray drying apparatus.

When developing DPI formulations, the API particle size (PS) required is usually between 0.5 and 5 μm. These APIs are often highly potent, which means that only a small dose is required to achieve the therapeutic effect, usually below 500 μg. Due to the API small particle size, the particles tend to be very cohesive due to their high surface free energy, which frequently leads to a poor aerosolization performance. Some of the strategies employed to mitigate this problem and to ensure improved delivery efficiency consist in the addition of excipients to manipulate the powder interfacial forces, in order to reduce the API cohesiveness and to avoid particle agglomeration, namely:

a) Blending the size-reduced API (0.5<PS<5 μm) with large carrier particles. The most commonly used and well-known carrier is lactose monohydrate. The API particles adhere to the carrier surface and upon oral inhalation of the formulation detach from the carrier surface. The particles are then deposited on the physiologically relevant stages of the lungs, while the carrier particles deposit at the mouth and throat. This method is known as "carrier-based";

b) Production of composite particles containing one or more excipients and one or more APIs. The composite particles are produced with a PS between 0.5 and 5 μm. The excipients are selected in order to reduce the particle cohesiveness in order to enable a good powder aerosolization. Upon inhalation, the particles flow through the respiratory tract and deposit in the physiologically relevant stages of the lungs. This is known as the "composite particle" method, where each particle comprises both excipient and drug.

Although both methods are used, the carrier-based method can present several drawbacks such as uniformity of the delivered dose issues and, sometimes, poor aerosolization efficiency (low fine particle fraction, that is, a low amount of API with an aerodynamic diameter of below 5 μm that is able to reach the deep lung). The use of the composite particles method has been gaining momentum, where the particles with a PS within 0.5 and 5 μm already contain the API and the excipients which improve the aerosolization and ensure a uniform API delivery to the lungs. Additionally, this method enables the processing of thermo-sensitive APIs such as biomolecules, since the particle engineering technologies employed are typically gentle. The production of composite particles using spray drying technology is a well-known formulation method that presents several advantages when compared with conventional encapsulating techniques like water-in-oil double emulsion and solvent evaporation coacervation methods. Although new encapsulating technologies like interfacial solvent exchange and dual-capillary electrospray have been used, the encapsulation process is still too complex. Spray drying is a simple, flexible, single step, optionally continuous and easily scalable process, with clear advantages over the previously described methods.

In a spray drying process, one or more components are dissolved or suspended in a solvent or mixture of solvents. In the conventional approach, the feedstock (comprising the excipients dissolved and the API dissolved or suspended, either in a single solvent or in a mixture of solvents) passes through a nozzle where the droplets are formed; and as the droplets contact with a hot gas stream, the solvent evaporates and dry particles are formed, which will be collected downstream through a cyclone, filter bag or any other suitable collecting system.

Generally accepted inhalation excipients, such as sugars, salts, amino acids, sugar alcohols, and polymers are usually water soluble and poorly soluble in the vast majority of the organic solvents that have practical application in spray drying. On the other hand, among the diversity of commercial APIs for inhalation as well as new chemical entities in research, the majority of the molecules exhibit poor water solubility. Furthermore, typical inhalation spray drying processes tend to favor aqueous feedstock to minimize the need for additional powder processing to comply with residual solvents limits. Hence, in order to perform spray drying of a pharmaceutical composition for inhalation:

1) there might be challenges to find a pharmaceutically acceptable solvent system that solubilizes both the API and the excipient(s);
2) even if point 1) can be overcome, some APIs may present chemical incompatibility towards the required mixture of aqueous and organic solvents and/or there might be limitations in terms of the maximum amount of API that can be solubilized, with a negative impact in process throughput and flexibility.
3) Although points 1) and 2) can be overcome by working with an API nanosuspension (that would be microencapsulated by the dissolved excipient phase, upon drying), size-reduction to the nano size range involves complex, expensive and laborious techniques that, in many cases, may prove unsuccessful.

When preparing a pharmaceutical composition for inhalation, by spray drying from a solution, the nozzles that are most commonly used are the two-fluid nozzles since the remaining types of nozzles (pressure, rotary and ultrasonic) are less efficient in generating the small droplet/particle size required. Several patents and articles contributed to the increased knowledge in the particle engineering field, which consisted in combinations of formulations and spray drying process parameters, enabling the production of inhalable pharmaceutical composite particles.

Four main patents contributed to the increasing knowledge regarding the combination of formulation and spray drying process parameter conditions. In the following patents, inhalable pharmaceutical powders were produced using a spray drying unit where the feed solution was delivered via a single feed stream.

Lipp et al., US2013/0266653 A1, refers to the production of spray dried respirable dry powder formulations for local or systemic delivery to the lungs of a pharmaceutical active agent containing one or more monovalent metal cation salts and optionally carbohydrates and/or amino acids as excipients. This patent provides methods to prepare dispersible composite particles. However, this method consists of the preparation of a single solution containing both API(s) and excipient(s) in a single solvent/co-solvent system, which limits the API/excipient system composition due to the solubility limitations of the selected solvent system.

In Mcintosh et al., WO 2013/016754 A1, the spray-drying of an aqueous solution and/or suspension comprising a biologically active protein or peptide, with one or more mono, di- or polysaccharides and/or amino acids, and L-leucine is claimed. The powders were able to reach high fine particle fractions (FPF) of about 73%. However, the process is limited to the spray drying of aqueous solutions containing preferably a biological active agent, indicating that there is no provision for preparing pharmaceutical active agents with poor water solubility.

In Vehring et al., U.S. Pat. No. 7,862,834 B2, a pharmaceutical dry powder formulation comprising an excipient encapsulating the active agent, where the excipient is more soluble in water than the active agent is claimed. Here, the formulation is produced using a solution comprising a first solvent, a second solvent, an active agent and an excipient where the second solvent is less polar than the first solvent; and, in this way, by removing the first and second solvents, particles comprising the active agent encapsulated by the excipient are yielded. In this invention, preferable encapsulating agents include L-leucine. However, in Vehring et al., the pharmaceutical dry powder inhaler composition limits the degree of encapsulation because a single solution comprising the API and excipient in a single solvent/co-solvent system is used. This decreases the process flexibility and the API/excipient system selection.

Vehring et al., U.S. Pat. No. 8,668,934 B2, claims a method of preparing a pharmaceutical formulation comprising: providing a single solution comprising a first solvent, a second solvent, an active agent and an excipient, where the second solvent is less polar than the first, and the excipient is more soluble in the first solvent than the active agent. In this patent, a single solution is delivered to the spray dryer for the production of encapsulated composite particles. In Vehring et al. the production method comprises the preparation of a single solution where the API and excipient(s) with different solubilities are all dissolved in a single solution using a single solvent/co-solvent system. This limits the range of API and excipient amount that can be incorporated in the solution, which in specific cases where the API is poorly water soluble can represent a hurdle for the production of inhalable composite particles.

The above-mentioned prior art patents are all based on spray drying pharmaceutical composite particles by delivering a single solution/suspension to the spray drying chamber, using a standard nozzle. These prior art patents share the same constraint, which is to dissolve the required amount of API(s) and excipient(s) with different solubility requirements in one solvent/co-solvent system, all in the same solution. This is particularly challenging for inhalation formulations since a large number of APIs present poor water solubility while the majority of the excipients are water soluble.

Alternatively, an external three-fluid nozzle has been used. Such external three fluid nozzles are composed by two liquid and one gas stream which are concentrically disposed to deliver the solutions outside the nozzle channels to the spray drying chamber. The three-fluid external nozzle is part of a new class of nozzles that are already known for the production of composite particles.

However, most of these applications are for oral or injectable purposes and most of them consist of spray drying the API particles in suspension, requiring the coupling of a size-reduction process to the spray drying process.

Kirkpatrick et al., U.S. Pat. No. 4,610,760, discloses a method of atomizing liquids, more specifically a three-fluid nozzle to atomize high viscosity and difficult-to-spherize liquids to be spray dried. However, the problem Kirkpatrick solves here is one of viscosity, which is overcome by using not one but two of the three-channels to deliver a gas stream. In this case there is no need to keep two solutions separate because only one exists.

York et al. [1], 1999, also describes a three-fluid nozzle used with supercritical fluids where a solution and a co-solvent are separately fed with the objective to control the crystallization mechanism and not partial particle encapsulation as in the present case.

Kondo et al. [2], discloses the production of sustained release microcapsules using a three-fluid nozzle. In this study, microparticles were prepared by spraying a drug suspension in the inner channel composed of an Ethenzamide (suspended API) and by Hypromellose 2910 (suspending agent) in water and an ethylcellulose solution in ethanol in the outer channel for coating. This case showed that the three-fluid nozzle is useful as a microencapsulation method when using suspended APIs with a suspending agent in the inner channel, however contrary to the present invention, it does not overcome the poor drug solubility challenge since the drug is suspended, which can also be performed using a two-fluid nozzle by controlling the solvents used and the drying kinetics.

Feng et al. [3], also makes use of a three-fluid nozzle where two of the channels are used to deliver solutions. One contains a water soluble protein (lysozyme) and a stabilizing sugar, both dissolved, and the second delivers dissolved poly lactic-co-glycolic acid (PLGA). As in Kondo et al. the objective is to perfectly coat and protect the protein and sugar core particles with the PLGA.

As described in connection with the previous authors, Pabari et al. [5] also describes the use of a three-fluid nozzle to produce diclofenac sodium (DFS) encapsulated by a polymer (ethyl cellulose) without reference to potential and unwanted solvent interactions.

Tanno et al., US 20050158386 A1 prepared a pharmaceutical solid dispersion using a three-fluid nozzle in a fluidized-bed granulation machine. The solid dispersion is produced by feeding into the inner channel a solution of a poorly soluble drug dissolved in a plasticizer and into the outer channel an aqueous solution and/or water dispersion of a water-soluble polymer. The goal of this strategy is to improve drug dissolution and the uniformity of granulations or coating films. This patent is distinct from the present invention where a glass former is used to stabilize the drug and the shell former improves the powder aerodynamic performance and enhances the drug protection; therefore focusing in a different field of application (inhalation delivery), ruled by different mechanisms and where very distinct challenges and goals are intrinsic.

In Gordon et al., US 20020132011 A1 a method of preparing dry powders with hydrophobic and hydrophilic components is presented using an internal mixture coaxial nozzle in a spray drying apparatus. In the invention, the two components are separately dissolved in different solvents and simultaneously directed to the coaxial nozzle, mixed in an internal chamber (internal mixture nozzle) and then delivered to the spray dryer drying chamber. However, the method of Gordon et al. presents potential problems such as: i) potential product precipitation and nozzle blockage inside the nozzle due to solubility or chemical incompatibility of the components; ii) liquid-liquid phase separations which may cause powder uniformity issues; and/or, iii) limited control over the powder properties (e.g. internal core and shell structure), and limited control over the encapsulation process.

Therefore, it is clear that the state of the art in the use of three-fluid nozzles is essentially concerned with encapsulation for protection purposes and not with the need to segregate different solutions so as to avoid limitations of optimum solubilisation.

It is also clear that the state of the art above does not provide teaching on using three-fluid nozzles for the preparation of pharmaceutical compositions of poorly water soluble active agents for inhalation purposes which requires very specific properties that the prior art does not provide.

In contrast, the present invention describes a production method where use of a three-fluid external mixing nozzle is essential, in that it keeps the two solutions apart, until the moment where they are co-spray dried, contrary to an internal mixing nozzle where both solutions are mixed inside the nozzle. Moreover, the present invention discloses a production method which consists of the use of an external three-fluid nozzle for the production of composite particles for inhalation purposes by delivering to the drying chamber two independent solutions that allow the control of the particle properties such as size, morphology and surface coating without the typical API/excipient solubility and/or chemical compatibility limitations.

The present invention overcomes some of the shortcomings identified in the art, by i) specifically addressing the API/excipients solubility limitations, which expands the API and excipients range than can be used, contributing for higher solids throughput since a more concentrated API/excipient solution can be prepared; ii) allows spray drying of compounds that are insoluble in the same solvent system; iii) allows spray drying of compounds that are chemically incompatible in the same solvent system; iv) enables a better control over the particles properties such as the microencapsulation degree; v) simplifies the overall process by eliminating the need to couple a size-reduction process with the active agent; vi) streamlines scale-up of the process; and vii) reduces the amount of organic solvents required to solubilize the active agent.

The present invention solves the problem of producing inhalation formulations where a large number of APIs present poor water solubility while the majority of the excipients are water soluble. It has been found to be advantageous to use two separate solutions, one for the API(s) and other for the excipient(s). It has been found to be advantageous to use an external three-fluid nozzle (i.e. two channels for the solutions and one for the drying gas) in the spray drying apparatus. Another advantage of the external three-fluid nozzle of the present invention is the fine control over the degree of encapsulation and higher flexibility by independently manipulating the API and excipient solutions composition and relative proportion fed to the spray dryer. The inhalable powders produced can be partially encapsulated, as observed in FIG. 1, where a different number of fragmented particles or particles with holes at the surface are observed across different trials/operating conditions. Controlling the degree of encapsulation is particularly advantageous for patients with acute lung disease conditions that demand a quick API burst on the target site, followed by a more sustained release.

Additionally, by using an external mixture nozzle, the mixing of the components occurs externally, thus enabling the use of higher solids content which is particularly critical and advantageous for the process throughput and economic viability, especially in the inhalation industry where the final product is extremely expensive.

SUMMARY OF THE INVENTION

The present invention relates a method of production of inhalable composite particles by spray drying two independent solutions comprising the API and excipient separately, by means of a three-fluid nozzle inside the drying chamber. This innovative concept allows spray drying of pharmaceutical compositions comprising API and excipients that are insoluble in the same solvent composition, enabling higher flexibility in terms of process parameters and final inhalable particle properties, while assuring the maintenance of an appropriate aerodynamic performance for pulmonary delivery, which would not be possible through a conventional spray drying process.

According to a first aspect of the present invention there is provided a method of preparing a pharmaceutical formulation, the method comprising: providing a first solution comprising a first solvent and an active agent, providing a second solution comprising a second solvent and at least one excipient; and removing the first and second solvents by simultaneously drying both the first and second solutions in a spray dryer having an external mixing three-fluid nozzle that produces one or more particles comprising both the active agent and the one or more excipient. In a preferred aspect the pharmaceutical composition is suitable for inhalation.

Preferably, the one or more excipient is more soluble in water than the active agent.

Preferably, the one or more particles have a mass median diameter of less than 5 μm. In particular, particles having a mass median diameter of between 0.5-5 μm, alternatively between 1-4 μm. The mass median diameter of the particles can be measured using a method known in the art such as use of a scanning electron microscope (SEM) or laser diffraction.

Preferably, the one or more particles comprise excipient at least partially encapsulating the active agent. The one or more particles may comprise excipient totally encapsulating the active agent.

At least one excipient is provided. One excipient may be a stabilizing agent. The at least one excipient may comprise one or more component chosen from the group comprising: amino acids; sugars; or mixtures thereof. The sugar may be selected from lactose, trehalose, or raffinose. The amino acid may be selected from leucine, iso-leucine, tri-leucine or isomers thereof. Any of the above-mentioned sugars may be combined with any of the above mentioned amino acids.

The excipient may comprise one or more components; preferably trehalose and leucine.

The first solvent may be an organic solvent or a mixture containing at least an organic solvent and water.

The second solvent may be water or a mixture containing at least water and an organic solvent.

The external three-fluid nozzle may comprise an inner channel and an outer channel, and preferably the first solution is fed to the inner channel and the second solution is fed to the outer channel. Alternatively, the first solution may be fed to the outer channel and the second solution fed to the inner channel. Alternative arrangements of external three-fluid nozzle as known in the art may also be used according to the method of the present invention.

Preferably, the feed rate of the second solution is always higher than the feed rate of the first solution. This ensures that the API is encapsulated or coated by the excipient.

Preferably, the active agent requires at least 30 parts of water to dissolve one gram of solid at a temperature of 20° C.

According to a second aspect of the present invention there is provided a pharmaceutical composition obtainable by the above-mentioned method.

BRIEF DESCRIPTION OF THE DRAWINGS

The present invention will now be described solely by way of example and with reference to the accompanying drawings in which:

FIG. 2: Scheme of a conventional laboratory scale spray dryer, equipped with a two-fluid nozzle.

FIG. 3: Scheme of a laboratory scale spray dryer applied in the example, equipped with a three-fluid nozzle.

Figure 4:
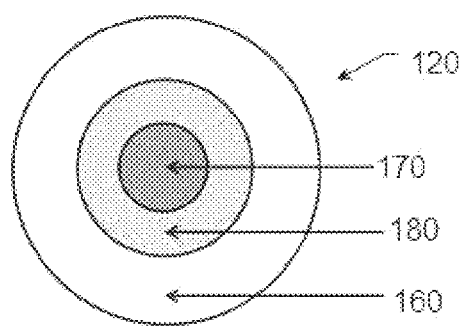
FIG. 4: Bottom view of the three-fluid nozzle internal distribution piping.

DETAILED DESCRIPTION OF THE INVENTION a) The invention makes use of a spray dryer apparatus equipped with a three-fluid nozzle as means to form particles from two independent solutions, as depicted in FIG. 3 and FIG. 4, which enables the production of composite particles for inhalation purposes with a good aerodynamic performance and without the solubility limitations observed when a single solution is prepared and the components present different solubility requirements.

b) As shown in FIG. 2, there is shown prior-art spray drying apparatus generally indicated (10) comprising an external two-fluid nozzle, generally indicated (20), which feeds into a drying chamber, generally indicated (30). Feeding into the external two-fluid nozzle (20) is an atomizing gas feed, generally indicated (22), and a liquid feed generally indicated (24). The nozzle (20) comprises two concentric flow paths. The first, outermost flow path comprises a first inlet linked to a first outlet. The second, innermost flow path comprises a second inlet linked to a second outlet. The atomizing gas feed (22) is linked to the first inlet, and the first fluid feed (24) is linked to the second inlet.

c) The drying chamber (30) is linked to a source of drying gas. Drying gas is circulated through the drying chamber (30) via a fan (34) via a heat exchanger (36), a condenser (38) and a cyclone (90).

d) The present invention is described in FIGS. 3 and 4. Some apparatus is equivalent to that of the prior art apparatus shown in FIG. 2, and in those instances like reference numerals are used. FIGS. 3 and 4 show spray drying apparatus according to the present invention generally indicated (100) comprising an external three-fluid nozzle, generally indicated (120), which feeds into a drying chamber, generally indicated (30). Feeding into the external three-fluid nozzle (120) is an atomizing gas feed, generally indicated (122), and a first liquid feed generally indicated (140) and a second liquid feed, generally indicated (150). The nozzle (120), as shown in FIGS. 3 and 4, comprises three concentric flow paths, generally indicated (160), (170) and (180). The first, outermost flow path comprises a first inlet (162) linked to a first outlet (164). The second, innermost flow path (170) comprises a second inlet (172) linked to a second outlet (174), and the third, middle flow path (180) comprises a third inlet (182) linked to a third outlet (184). The atomizing gas feed (122) is linked to the first inlet (162), the first fluid feed (140) is linked to the second inlet (172) and the second fluid feed (150) is linked to the third inlet (182).

e) The drying chamber (30) is linked to a source of drying gas. Drying gas is circulated through the drying chamber (30) via a fan (34) via a heat exchanger (36), a condenser (not shown) and a cyclone (90).

f) In the spray-drying process, the two different liquid feed streams (140 and 150) are concentrically delivered to the drying chamber (30) and are atomized into droplets due to the atomizing gas feed (122). When these droplets enter the drying chamber (30), along with co-current drying gas, the droplets undergo an evaporation process in which the solvent(s) are removed, forming a dry powder that is afterwards carried by the gas and collected in the cyclone (90) (or other collecting system such as a filter bag or a electrostatic precipitator).

g) By using the three-fluid nozzle approach, there are no component solubility limitations, since two separate solutions are prepared and concentrically delivered to the nozzle (120), which allows more flexibility on the spray drying parameters and formulation composition choice and potentially higher solids throughput.

h) The inner feed (140) can comprise the API dissolved in a solvent or mixture of solvents at a given concentration of solids (C_solids_in) while the outer feed (150) can comprise the excipient(s) dissolved at a given concentration of solids (C_solids_out) in a solvent or solvents mixture.

i) Each channel can deliver a solution or suspension, but preferably a solution.

j) An appropriate aerodynamic performance of the inhalable composite particles is determined by the combination of the optimal formulation composition and the spray drying process parameters, namely solvent composition, first liquid feed (140), second liquid feed (150), C_solids_in, C_solids_out, T_out and atomization gas flow (122), amongst others.

k) The current invention is particularly advantageous for preparing pharmaceutical compositions of poorly water soluble APIs. Herein, poorly water soluble APIs are defined as any active substance that will require at least 30 parts of water to dissolve one gram of solid at a temperature of 20° C.

The main advantages of the present invention include:
No solubility limitations for the API(s)/excipient(s) since two independent solutions/suspensions are prepared;
Higher process flexibility since an individual control of each feed flow rate (140, 150) and composition can be performed;
Higher process throughput since there are no solubility limitations for the API while maintaining a good aerodynamic performance.
Better control over the coating/encapsulation degree of the API;
Lower final residual organic solvent content since the solvent quantities required to dissolve the API would be lower when compared with the standard two-fluid nozzle;
Simpler process when comparing with other conventional encapsulating methodologies.

As used herein, "API" includes any physiologically or pharmacologically active substance that produces a localized or systemic effect in a patient. The active agent can comprise but is not limited to, for example, antibiotics, antifungal agents, antiviral agents, anepileptics, analgesics, anti-inflammatory agents, bronchodilators, and viruses and may be inorganic and organic compounds, including, without limitation, drugs which act on the peripheral nerves, adrenergic receptors, cholinergic receptors, the skeletal muscles, the cardiovascular system, smooth muscles, the blood circulatory system, synaptic sites, neuroeffector junctional sites, endocrine and hormone systems, the immunological system, the reproductive system, the skeletal system, autacoid systems, the alimentary and excretory systems, the histamine system and the central nervous system. Suitable agents may be selected from, for example, polysaccharides, steroids, hypnotics and sedatives, psychic energizers, tranquilizers, anticonvulsants, muscle relaxants, antiparkinson agents, anti-inflammatories, muscle contractants, antimicrobials, antimalarials, hormonal agents including contraceptives, sympathomimetics, polypeptides, and proteins capable of eliciting physiological effects, diuretics, lipid regulating agents, antiandrogenic agents, antiparasitics, neoplastics, antineoplastics, hypoglycemics, nutritional agents and supplements, growth supplements, fats, antienteritis agents, electrolytes, vaccines and diagnostic agents.

The active agent of the present invention may be combined with pharmaceutical carriers or excipients. These excipients can be used as bulking agents or to improve coating and/or to improve the stability and/or dispersibility of the powder. The excipients can be delivered via pulmonary route, with or without the active agent, for example, in placebo trials. The excipients include but are not limited to carbohydrates, amino acids, salts, peptides and proteins, alditols, biodegradable polymers, surfactants, amongst others. The solvent/solvents system used can comprise but are not limited to water, organic acids, such as acetic acid, an alcohol, an amine, an aldehyde, a ketone, an ester, a halide, an aromatic, and/or an alkane.

EXAMPLE

The aerodynamic performance and the drug uniformity results of the experiments described below demonstrate a successful proof-of-concept for the current invention and is not limiting of the same.

In these experiments the conventional two-fluid nozzle (1 liquid and 1 gas channel)—as shown in FIG. 2—was substituted by a three-fluid nozzle (2 liquid and 1 gas channel) in the spray drying apparatus as shown in FIG. 3. The two fluids and gas are delivered concentrically as shown in FIG. 3 and FIG. 4. Two separate solutions were prepared. Solution 1 was prepared by dissolving the API, fluticasone propionate (FP), in an ethanol system, while solution 2 was prepared by dissolving trehalose and L-leucine (80:20 w/w) in a water/ethanol system (50:50 v/v), to be delivered through the inner and outer liquid channels, respectively.

A laboratory scale spray dryer (BUCHI model B-290 Advanced) was used to process the above feed solutions (solution 1 and solution 2). In all trials, the BUCHI unit was equipped with a single external three-fluid nozzle with an inner feed orifice diameter of 0.7 mm, outer feed orifice diameter of 2.0 mm and cap with 2.8 mm of diameter. The F_drying gas and F_feed of the first solution (140) was kept constant at 35 kg/h and 1 mL/min, respectively.

In Trials #1, #2, #3, several process/formulation parameters were kept constant—Table 1. The composition of solution 1 and solution 2 remained unaltered, as well as the rotameter and the feed flow of the first fluid solution (solution 1) (140) and the feed flow of the second fluid feed solution (solution 2) (150). The spray drying conditions used in trial #1 are presented in Table 1. In trial #2, the effect of decreasing the outlet temperature of the drying gas (T_out) was evaluated, T_out ~65° C. In trial #3, the impact of decreasing the amount of atomization gas was assessed by decreasing the atomization gas flow from 60 to 45 mm in the rotameter, while maintaining the T_out at 95° C.

In trial #4, the API percentage relative to the total solids was of 5% w/w. To evaluate the API powder uniformity, 5 samples of 100±0.1 mg were weighted and dissolved in a 100 mL volumetric flask. The API content uniformity was assessed and it was observed that the API uniformity is ensured, obtaining a relative standard deviation (RSD) of 1.27%. According to these RSD results, it may be assumed that all trials that contain 1% of the total solids of FP API are uniformly dispersed in the particles formed.

In trial #5, the second fluid feed (150) was increased from 4 to 10 mL/min to assess the impact on the powder aerodynamic performance.

To assess the powder aerodynamic performance, a Fast Screening Impactor (FSI) was used to determine fine particle fraction (FPF) of the generated composite particles. Hypromellose (HPMC) size 3 capsules were hand filled with 20 mg of powder and were actuated using a Plastiape RH model 7 at 60 L/min, 4 kPa. The tests were performed in duplicate.

Trials #1, #2 and #4 returned FPF values, relative to the powder emitted dose (FPFED), from 76 up to 86%, showing an aerodynamic performance suitable for pulmonary delivery. The preparation of two individual solutions enabled the production of composite particles without any solubility limitations from the API and excipients point-of-view, while maintaining a good process yield. If a single solution was prepared, a careful balance between the solvents ratio and the API/excipients concentration would be required with clear composition limitations.

Based on the FPFED values of trials #2 and #5, it can be concluded that lower atomization and higher second fluid feed values tend to promote lower aerodynamic performance.

Figure 1:
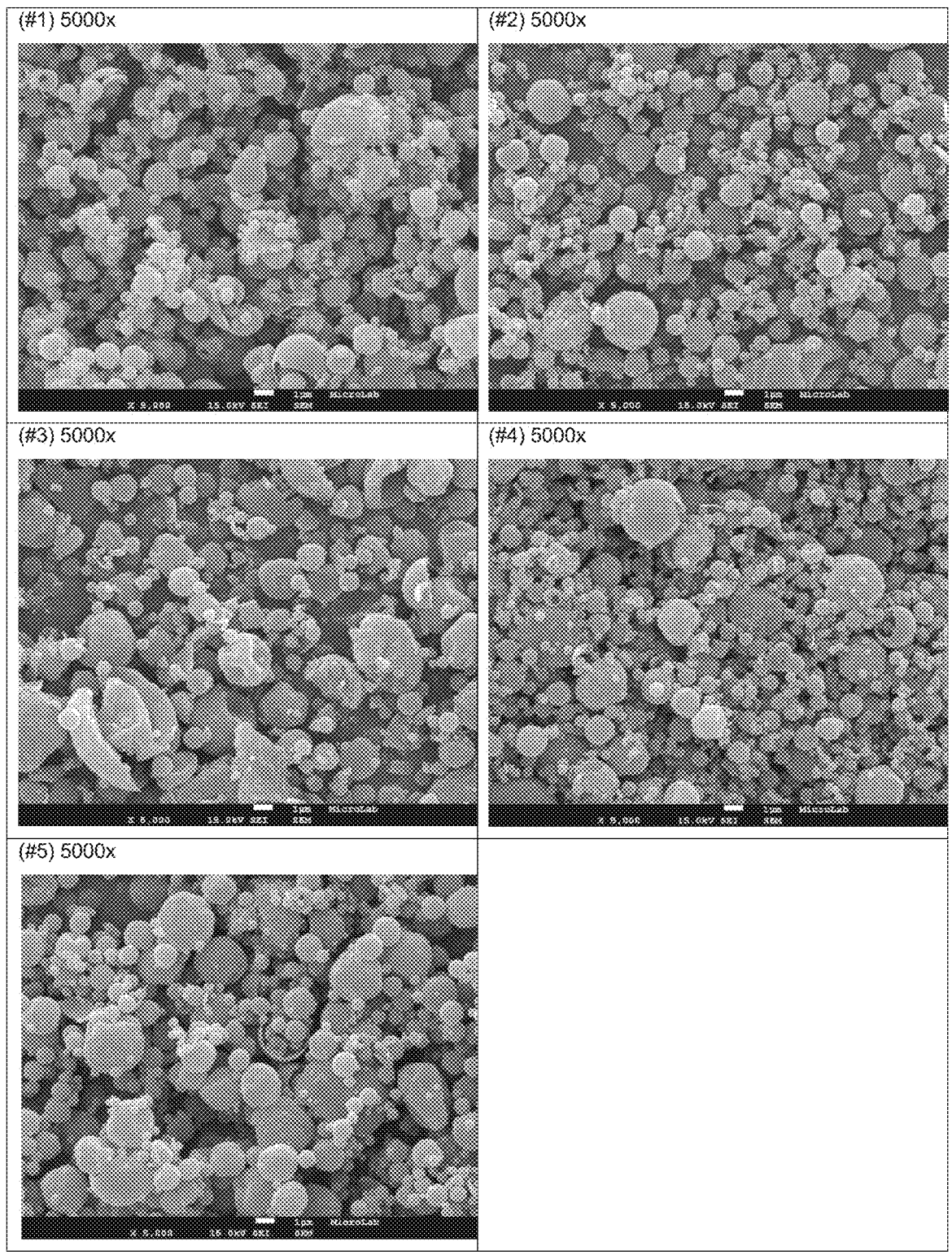
FIG. 1: SEM micrographs of the dry particles produced using the three-fluid nozzle under the different production conditions: Trial #1 to #5.

The SEM images of the powders produced are presented in FIG. 1. Based on the SEM micrographs of all 5 trials, it is possible to observe that all particles are within the inhalable range (particle size below 5 μm) and that in all cases, fragmented particles or particles with an opening at the surface are observed.

| Trial | | #1 | #2 | #3 | #4 | #5 |
|---|---|---|---|---|---|---|
| First fluid solution | mL/min | 1 | 1 | 1 | 1 | 1 |
| C_solids_in (ethanol) | % w/v | 0.08 | 0.08 | 0.08 | 0.4 | 0.18 |
| Second fluid solution | mL/min | 4 | 4 | 4 | 4 | 9 |
| C_solids_out (water/ethanol) (50:50) | % w/v | 2 | 2 | 2 | 1.9 | 0.4 |
| Rotameter | mm | 60 | 60 | 45 | 60 | 60 |
| T_out | ° C. | 95 | 65 | 95 | 65 | 65 |
| Powder Properties | | | | | | |
| $FPF_{ED}$ (FSI; n = 2) | % | 79.1 | 86.3 | 50.6 | 76.2 | 73.7 |
| Process yield | % | 72.1 | 82.4 | 83.1 | 72.3 | 70.1 |

Note:
F_drying—drying gas flow rate; first fluid solution—solution flow rate from the inner channel; second fluid solution—solution flow rate from the outer channel; C_solids_in—concentration of solids in the inner channel solution; C_solids_out—concentration of solids in the outer channel solution; T_out—outlet temperature of the drying gas; $FPF_{ED}$—fine particle fraction relative to the emitted dose from the capsule.

These results support the concept that, by using a three-fluid nozzle, particles with a high FPF and a uniform API content can be obtained. In all cases, a higher or smaller number of fragmented particles were observed. The production method of these particles is not limited by the API(s)/excipient(s) solubility. Hence, the results herein presented demonstrate the success of the current proof-of-concept and, in this way, the feasibility of using a three-fluid nozzle for the production of composite particles, capable of fulfilling all the previous aims and goals.

REFERENCES

[1] S. Palakodaty and P. York, "Phase behavioral effects on particle formation processes using supercritical fluids," *Pharm. Res.*, vol. 16, no. 7, pp. 976-985, 1999.
[2] K. Kondo, T. Niwa, and K. Danjo, "Preparation of sustained-release coated particles by novel microencapsulation method using three-fluid nozzle spray drying technique," *Eur. J. Pharm. Sci.*, vol. 51, pp. 11-19, 2014.
[3] F. Wan, M. J. Maltesen, S. K. Andersen, S. Bjerregaard, C. Foged, J. Rantanen, and M. Yang, "One-Step Production of Protein-Loaded PLGA Microparticles via Spray Drying Using 3-Fluid Nozzle.," *Pharm. Res.*, no. 10, February 2014.
[4] J. Legako and N. T. Dunford, "Effect of spray nozzle design on fish oil-whey protein microcapsule properties," *J. Food Sci.*, vol. 75, no. 6, 2010.
[5] R. M. Pabari, T. Sunderland, and Z. Ramtoola, "Investigation of a novel 3-fluid nozzle spray drying technology for the engineering of multifunctional layered microparticles," *Expert Opin. Drug Deliv.*, pp. 1-12, 2012.

The invention claimed is:

1. A method of preparing a dry powder inhalation pharmaceutical formulation, the method comprising: providing a first solution comprising a first solvent and an Active Pharmaceutical Agent (API), wherein the API is an active agent which requires at least 30 grams of water to dissolve one gram of solid at a temperature of 20° C.; providing a second solution comprising a second solvent and at least one excipient; and removing the first and second solvents by simultaneously drying both the first and second solutions in a spray dryer having an external mixing three-fluid nozzle that produces one or more particles comprising both the API and the at least one excipient; wherein the first solvent is a different solvent to the second solvent, wherein the first solvent is an organic solvent or a mixture containing at least an organic solvent and water and wherein the second solvent is water or a mixture containing at least water and an organic solvent, wherein the at least one excipient is more soluble in water than the API, wherein the API is more soluble in the organic solvent than the at least one excipient, and wherein the at least one excipient comprises one or more component selected from the group consisting of: amino acids; sugars; and mixtures thereof.

2. The method according to claim 1, wherein the one or more particles have a mass median diameter of less than 5 μm.

3. The method according to claim 1, wherein the one or more particles comprise the at least one excipient at least partially encapsulating the active agent.

4. The method according to claim 1, wherein the one or more particles comprise the at least one excipient totally encapsulating the active agent.

5. The method according to claim 1, wherein the at least one excipient is a stabilizing agent.

6. The method according to claim 1, wherein the sugars are selected from lactose, trehalose, or raffinose.

7. The method according to claim 1, wherein the amino acids are selected from leucine, iso-leucine, tri-leucine or isomers thereof.

8. The method according to claim 1, wherein the at least one excipient comprises trehalose and leucine.

9. The method according to claim 1, wherein the external mixing three-fluid nozzle comprises an inner channel and an outer channel, and wherein the first solution is fed to the inner channel and the second solution is fed to the outer channel.

10. The method according to claim 1, wherein the feed rate of the second solution is always higher than the feed rate of the first solution.

11. A pharmaceutical composition obtained by the method according to claim 1.

12. The method according to claim 2, wherein the sugars are selected from lactose, trehalose, or raffinose.

13. The method according to claim 2, wherein the amino acids are selected from leucine, iso-leucine, tri-leucine or isomers thereof.

14. The method according to claim 2, wherein the at least one excipient comprises trehalose and leucine.

15. The method according to claim 9, wherein the sugars are selected from lactose, trehalose, or raffinose.

16. The method according to claim 9, wherein the amino acids are selected from leucine, iso-leucine, tri-leucine or isomers thereof.

17. The method according to claim 9, wherein the at least one excipient comprises trehalose and leucine.

18. The method according to claim 15, wherein the feed rate of the second solution is always higher than the feed rate of the first solution.

19. The method according to claim 16, wherein the feed rate of the second solution is always higher than the feed rate of the first solution.

20. The method according to claim 17, wherein the feed rate of the second solution is always higher than the feed rate of the first solution.

* * * * *